United States Patent [19]
Hanagata et al.

[11] Patent Number: 5,831,079
[45] Date of Patent: Nov. 3, 1998

[54] METHOD OF PREPARING GANGLIOSIDE

[76] Inventors: Goro Hanagata, 2-18-17 Fujimi,Saitama 350-13, Sayama-shi; Susumu Miura, 5-11-3 Arajukucho, Saitama 350, Kawagoe-shi; Kiyoshi Tatsumi, 982-2, Noda, Saitama 358, Iruma-shi, all of Japan

[21] Appl. No.: 534,941

[22] Filed: Sep. 28, 1995

[30] Foreign Application Priority Data

Sep. 30, 1994 [JP] Japan .................................. 6-2161035

[51] Int. Cl.⁶ ...................................................... C07H 1/00
[52] U.S. Cl. ................................ 536/124; 536/53; 514/61
[58] Field of Search .......................... 536/53, 124; 514/61

[56] References Cited

FOREIGN PATENT DOCUMENTS 2662697  12/1991  France .
2-207090  8/1990  Japan .
5-279379  10/1993  Japan .
5-304955  11/1993  Japan .

OTHER PUBLICATIONS

*Laegreid et al. J. Chromatogr,* 1986, 377, 59–67.

*Primary Examiner*—Kathleen K Fonda

[57] ABSTRACT

A method of preparing Ganglioside $G_{M3}$ which comprises converting Ganglioside $G_{D3}$ into Ganglioside $G_{M3}$ in an alkaline condition is disclosed. The conversion of Ganglioside $G_{D3}$ into Ganglioside $G_{M3}$ is preferably carried out by thermal treating Ganglioside $G_{D3}$ in an alkaline condition. The thermal treatment is preferably carried out at a pH ranging from 8 to 11 and at a temperature ranging from 30° C. to 140° C.

7 Claims, 2 Drawing Sheets

METHOD OF PREPARING GANGLIOSIDE

BACKGROUND OF THE INVENTION

1. Field of the Invention

The present invention relates to a method of preparing Ganglioside. In particular, the present invention relates to a method of Ganglioside $G_{M3}$ by hydrolyzing Ganglioside $G_{D3}$ with an alkali.

The Ganglioside $G_{M3}$ prepared by the method of the present invention is useful as a reagent used in medical, pharmaceutical and biochemical fields, and is also useful as a material for pharmaceuticals, cosmetics, foods, beverages and animal feeds.

2. Description of the Prior Art

Ganglioside is a general name of sphingoglycolipid having sialic acid, and the existence of various molecular species thereof are known. Among them, Ganglioside $G_{M3}$ has a structure in which reducing terminal of lactose bonds to a ceramide and a sialic acid $\alpha 2$–$3$ bonds to nonreducing terminal of the lactose. Ganglioside $G_{D3}$ has a structure in which a further sialic acid $\alpha 2$–$8$ bonds to nonreducing terminal of Ganglioside $G_{M3}$, and thus the whole molecule of Ganglioside $G_{D3}$ has two molecules of sialic acid.

As for Ganglioside $G_{M3}$, various physiological functions have been known, and for example proliferation inhibiting function of keratinocyte, angiogenic repressing function and differentiation function of leukocyte have been reported. In addition, Ganglioside $G_{M3}$ has been known to be a receptor to influenza or Newcastle disease viruses.

As a method of preparing Ganglioside $G_{M3}$ from Ganglioside $G_{D3}$, a method of hydrolyzing Ganglioside $G_{D3}$ with sialidase or with an acid is known (Japanese Patent Application (OPI) No. 5-279379). However, the method of hydrolyzing with sialidase is not always considered to be a industrially advantageous method, since Ganglioside is inhibited by coexisting proteins, substrates are easily inhibited by coexisting free sialic acid and bonding sialic acid and the like, and the sialidase used is expensive. In addition, with the method of hydrolyzing with an acid, precipitates of proteins are easily produced although the cost needed for the conversion is low. It is, therefore, very difficult to apply this method to a raw material containing a high amount of proteins such as bovine milk or milk products. Further, there is a problem that viscosity of solution is easily increased when hydrolyzed with an acid.

It has been generally known that precipitates of proteins are not produced and viscosities are not increased with an alkali. However, bonds of sugars are stable against alkalis, and desialyzing reaction with an alkali was difficult.

SUMMARY OF THE INVENTION

The present inventors have researched a method of preparing Ganglioside $G_{M3}$ from Ganglioside $G_{D3}$ to find out that Ganglioside $G_{D3}$ may be converted into Ganglioside $G_{M3}$ by treating Ganglioside $G_{D3}$ in a specific alkaline condition to desialize only one sialic acid molecule bonded to nonreducing terminal of sialic acid moiety of Ganglioside $G_{D3}$, and thus completed the present invention.

Under such circumstances, an object of the present invention is to provide a method of preparing Ganglioside $G_{M3}$ by converting Ganglioside $G_{D3}$ into Ganglioside $G_{M3}$ in an alkaline condition in which precipitates of proteins and the like are not produced.

In accordance with the present invention, there is provided a method of preparing Ganglioside $G_{M3}$ which comprises converting Ganglioside $G_{D3}$ into Ganglioside $G_{M3}$ in an alkaline condition.

In accordance with the present invention, there is provided a method of preparing Ganglioside $G_{M3}$ wherein said conversion of Ganglioside $G_{D3}$ into Ganglioside $G_{M3}$ is carried out by thermal treating Ganglioside $G_{D3}$ in an alkaline condition.

In accordance with the present invention, there is provided a method of preparing Ganglioside $G_{M3}$ wherein said thermal treatment of Ganglioside $G_{D3}$ is carried out at a pH ranging from 8 to 11 and at a temperature ranging from 30° C. to 140° C.

DETAILED DESCRIPTION OF THE PREFERRED EMBODIMENTS

The features of the method of the present invention is to convert Ganglioside $G_{D3}$ into Ganglioside $G_{M3}$ in an alkaline specific condition. In other words, it is very important to set the reaction pH and the reaction temperature in the method of the present invention. The higher reaction pH and the higher reaction temperature, the higher production rate of Ganglioside $G_{M3}$ becomes but the higher decomposition rate of Ganglioside $G_{M3}$ becomes. Thus the reaction pH is preferably set to in the range from 8 to 11, more preferably set to in the range from 8 to 10, and the reaction temperature is preferably set to in the range from 30° C. to 140° C., more preferably set to in the range from 75° C. to 100° C. in order to obtain Ganglioside $G_{M3}$ in a high yield. A reaction time may be set depending on the reaction conditions suitably.

In the method of the present invention, Ganglioside $G_{D3}$ is used as a starting material. The starting material may be a highly purified Ganglioside $G_{D3}$; a material containing a relatively high amount of Ganglioside $G_{D3}$ such as whey protein concentrate (WPC) or butter milk; a material containing a high amount of proteins but not a high amount of Ganglioside $G_{D3}$ such as whole milk or delipidated milk; or an extract obtained by extracting from a material containing Ganglioside $G_{D3}$ with an organic solvent such as ethanol (Japanese Patent Application (OPI) No. 2-207090)).

The Ganglioside $G_{M3}$ thus obtained may be separated and purified by a conventional method to be used as a reagent, and may be used as a material for pharmaceuticals, cosmetics, foods, beverages or animal feeds in a form of a composition containing Ganglioside $G_{M3}$.

Thus the method of the present invention is useful as an industrial method of preparing Ganglioside $G_{M3}$ since Ganglioside $G_{M3}$ can be prepared from Ganglioside $G_{D3}$ relatively inexpensively and simply by the method of the present invention.

The following examples are further illustrative of the present invention, and are not to be construed as limiting the scope thereof. Unless expressly indicated to be otherwise, all parts and percentages are by weight.

EXAMPLE

Example 1

5 N sodium hydroxide was added to an aqueous solution of 10% whey protein concentrate (WPC) containing 130 mg/L of Ganglioside $G_{D3}$ to set pH of the mixture to 9.7.

Figure 1:
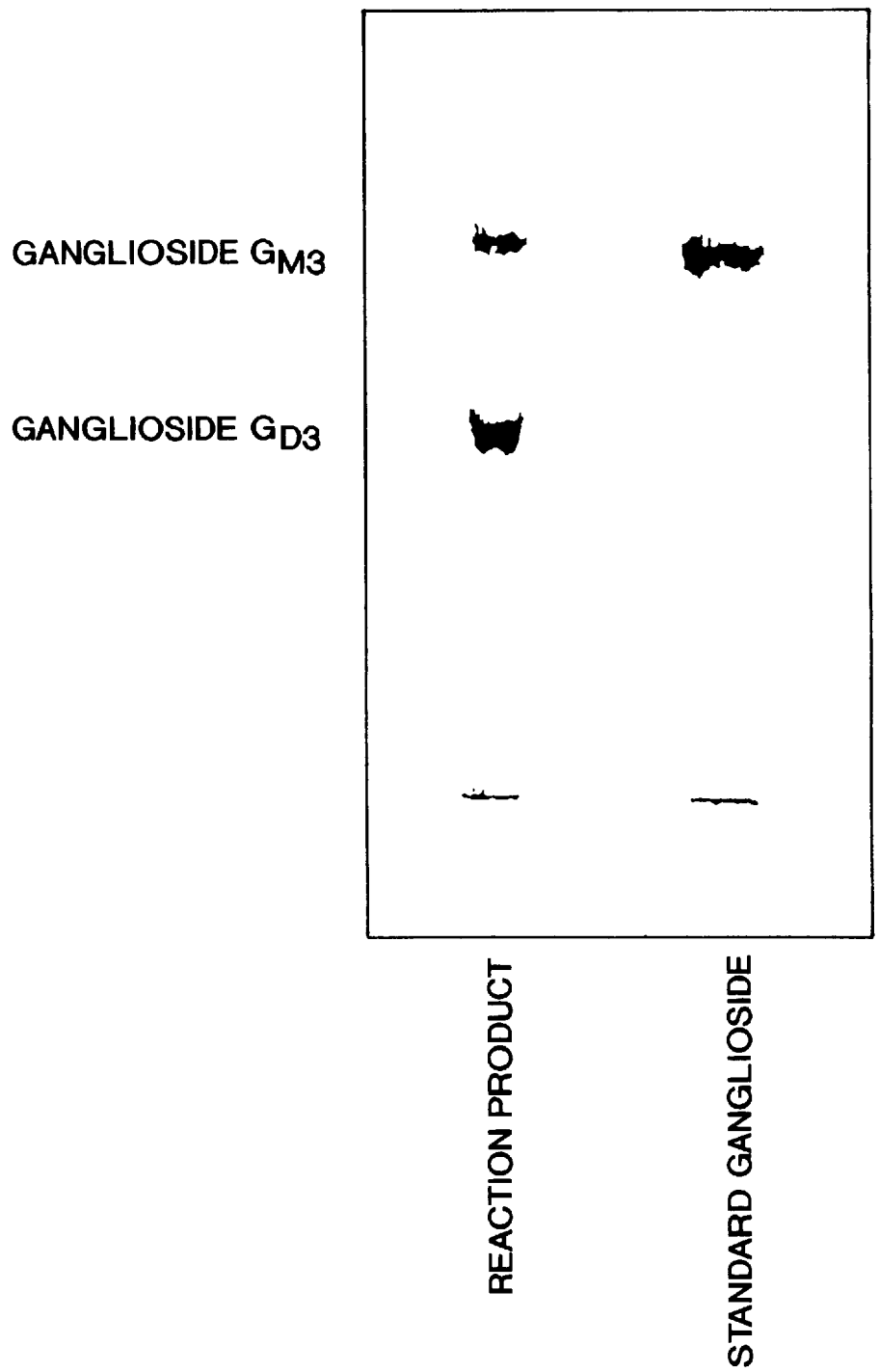
FIG. 1 shows a result of thin layer chromatography of the reaction product obtained in EXAMPLE 1.

Then the mixture was reacted at 85° C. for 60 minutes. At that time, precipitate was not produced in the reaction mixture, and viscosity was not increased. After completing the reaction, the reaction mixture was neutralized by adding 2 N hydrochloric acid to the reaction mixture. After extracting a lipid fraction by a solvent (chloroform:methanol=2:1, by vol.), the lipid fraction was followed by thin layer chromatography (No.13749; obtained from Merck). The thin layer chromatography was developed using a solvent (chloroform:methanol:$H_2O$=60:35:8,by vol.) and was color developed with resorcinol. The results were as shown in FIG. 1. It was proved that Ganglioside $G_{M3}$ having the same Rf value as Ganglioside $G_{M3}$ derived from bovine brain as a standard. In addition, it was confirmed that the reaction mixture contained 42 mg/L of Ganglioside $G_{M3}$ by a densitometry.

Example 2

2 L of 80% ethanol was added to 100 g of butter milk powder and the mixture was stirred at room temperature for 8 hours. Then precipitates were removed by filtration. Water was added, and the mixture was distilled under a reduced pressure repeatedly at a low temperature to remove ethanol to obtain 2 L of an aqueous solution finally which was used as a starting material. The aqueous solution contained 2.6 g/L of Ganglioside $G_{D3}$ and 0.16 g/L Ganglioside $G_{M3}$.

2 N potassium hydroxide was added to the aqueous solution to set pH of the mixture to 8. Then the mixture was reacted at 95° C. for 60 minutes. After completing the reaction, the reaction mixture was neutralized by adding 2 N hydrochloric acid to the reaction mixture. After extracting a lipid fraction by a solvent (chloroform:methanol=2:1,by vol.), the lipid fraction was followed by a thin layer chromatography as described in EXAMPLE 1. As the results, it was confirmed that the reaction mixture contains 0.72 g/L of Ganglioside $G_{M3}$.

Figure 2:
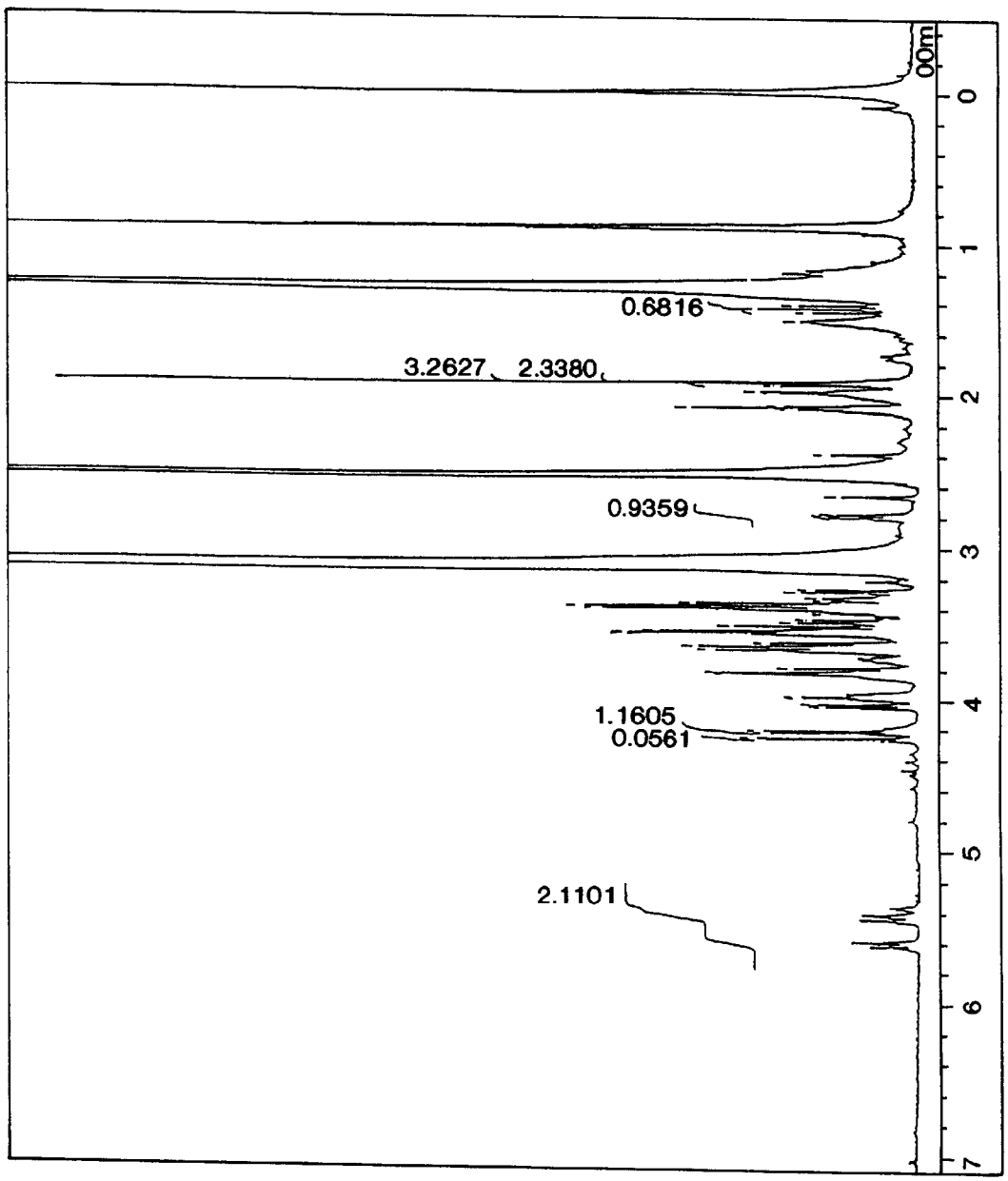
FIG. 2 shows a NMR spectrum of the reaction product obtained in EXAMPLE 2.

The fraction corresponding to Ganglioside $G_{M3}$ was extracted by a solvent (chloroform:methanol=2:1,by vol.) and was dried under a reduced pressure to obtain white powder. The powder was followed by ion-exchange chromatography with DEAE-Sephadex A-25 (obtained from Pharmacia) and was followed by silica gel chromatography by Iatrobeads 6RS 8060 (obtained from Iatro Laboratories, Inc.) to collect a reaction product. After freeze drying the product, 0.68 g of the obtained white powder was analyzed with NMR, a result as shown in FIG. 2 was obtained. The result corresponded to the standard.

Example 3

1 N sodium hydroxide was added to 5 L of skim milk containing 3.8 mg/L of Ganglioside $G_{D3}$ and 0.1 mg/L of Ganglioside $G_{M3}$ to set pH of the mixture to 8.7. Then the mixture was reacted at 90° C. for 60 minutes. After completing the reaction, the reaction mixture was neutralized by adding 0.5 N hydrochloric acid. After extracting a lipid fraction by a solvent (chloroform:methanol=2:1,by vol.), the lipid fraction was followed by thin layer chromatography as described in EXAMPLE 1. As the results, it was confirmed that the reaction mixture contained 1.1 mg/L of Ganglioside $G_{M3}$.

By the present invention, Ganglioside $G_{M3}$ can be prepared from Ganglioside $G_{D3}$ inexpensive and simple manner. In particular, since Ganglioside $G_{M3}$ can be prepared from a raw material such as milk and milk products containing relatively high amounts of proteins, the method of the present invention is useful as a industrial method for preparing Ganglioside $G_{M3}$. The Ganglioside $G_{M3}$ prepared by the method of the present invention has physiological functions such as infection protective ability, and thus it is useful as a material for pharmaceuticals, cosmetics, foods and beverages and animal feeds.

The foregoing examples and description of the preferred embodiment should be taken as illustrating, rather than as limiting, the present invention as defined by the claims. As will be readily appreciated, numerous variations and combinations of the features set forth above can be utilized without departing from the present invention as set forth in the claims. Such variations are not regarded as a departure from the spirit and scope of the invention, and all such modifications are intended to be included within the scope of the following claims.

We claim:

1. A method of preparing Ganglioside $G_{M3}$ which consists essentially of (a) adjusting the pH of a material containing Ganglioside $G_{D3}$ to a pH ranging from 8 to 11, and then (b) thermally treating the material at a temperature ranging from 30° to 140° C.

2. The method of preparing Ganglioside $G_{M3}$ as claimed in claim 1, wherein the thermal treatment is carried out at a temperature ranging from 75° to 100° C.

3. The method of preparing Ganglioside $G_{M3}$ as claimed in claim 1, wherein the pH is adjusted to a pH ranging from 8 to 10.

4. The method of preparing Ganglioside $G_{M3}$ as claimed in claim 1, wherein the pH is adjusted to a pH ranging from 8 to 10, and the thermal treatment is carried out at a temperature ranging from 75° to 100° C.

5. The method of preparing Ganglioside $G_{M3}$ as claimed in claim 1, wherein the material containing Ganglioside $G_{D3}$ is a purified Ganglioside $G_{D3}$, or an extract obtained by extracting a material containing Ganglioside $G_{D3}$ with an organic solvent.

6. The method of preparing Ganglioside $G_{M3}$ as claimed in claim 1, wherein the material containing Ganglioside $G_{D3}$ is whey protein concentrate (WPC) or buttermilk.

7. The method of preparing Ganglioside $G_{M3}$ as claimed in claim 1, wherein the material containing Ganglioside $G_{D3}$ is whole milk or delipidated milk.

* * * * *

UNITED STATES PATENT AND TRADEMARK OFFICE
CERTIFICATE OF CORRECTION

PATENT NO. : 5,831,079
DATED : Nov. 3, 1998
INVENTOR(S) : Goro Hanagata, et al

It is certified that error appears in the above-identified patent and that said Letters Patent is hereby corrected as shown below:

On title page, item [30], should read as follows:
"6-2161035" should read --6-261035--

Signed and Sealed this

Twenty-ninth Day of June, 1999

Attest:

Q. TODD DICKINSON

*Attesting Officer*          *Acting Commissioner of Patents and Trademarks*